United States Patent [19]

Reiffen et al.

[11] Patent Number: 4,584,293

[45] Date of Patent: Apr. 22, 1986

[54] AMINOTETRALIN DERIVATIVES

[75] Inventors: Manfred Reiffen, Biberach; Joachim Heider, Warthausen; Volkhard Austel; Norbert Hauel, both of Biberach, all of Fed. Rep. of Germany; Walter Kobinger; Christian Lillie, both of Vienna, Austria

[73] Assignee: Dr. Karl Thomae GmbH, Biberach an der Riss, Fed. Rep. of Germany

[21] Appl. No.: 732,199

[22] Filed: May 8, 1985

[30] Foreign Application Priority Data

May 17, 1984 [DE] Fed. Rep. of Germany ....... 3418270

[51] Int. Cl.⁴ .................... A61K 31/55; C07D 223/16; C07D 491/55; C07D 521/00
[52] U.S. Cl. .................................. 514/213; 514/221; 260/239.3 B; 260/239.3 T; 260/239 BB; 260/239 BD; 549/433
[58] Field of Search .................. 260/239.3 B, 239.3 T; 514/213, 221

[56] References Cited

U.S. PATENT DOCUMENTS 4,490,369 12/1984 Reiffen et al. ................ 260/239.3 B Primary Examiner—Robert T. Bond
Attorney, Agent, or Firm—David E. Frankhouser; Charles J. Herron; Alan R. Stempel

[57] ABSTRACT

This invention related to new aminotetralin derivatives of formula I

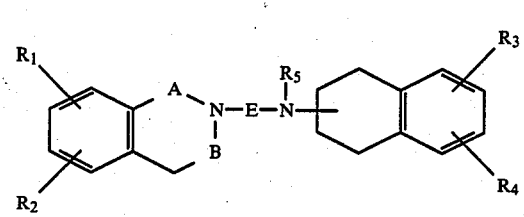

wherein

A is $-CH_2-CH_2-$, $-CH=CH-$, $-NH-CO-$,
$\phantom{5555555}5$ $-CH_2-CO-$, $-CO-CO-$ or $-CHOH-CO-$;
$\phantom{55}5\phantom{555555555555555555}5$ B is methylene or, when A is $-CH_2-CH_2-$, $-CH=CH-$, $-NH-CO-$ or $-CH_2-CO-$, B can also be carbonyl or thiocarbonyl;

E is a $C_2-C_4$ straight-chain alkylene, optionally substituted by a $C_1-C_3$ alkyl, or is 2-hydroxy-n-propylene, 2-hydroxy-n-butylene or 3-hydroxy-n-butylene;

$R_1$ is hydrogen, fluorine, chlorine, bromine, trifluoromethyl, nitro, amino, $C_1-C_3$ alkylamino, $C_1-C_3$ dialkylamino, $C_1-C_3$ alkyl, $C_1-C_3$ alkylthio, hydroxy, $C_1-C_3$ alkoxy or phenyl $C_1-C_3$ alkoxy;

$R_2$ is hydrogen, chlorine, bromine, hydroxy, $C_1-C_3$ alkoxy phenyl $C_1-C_3$ alkoxy, or $C_1-C_3$ alkyl or, together with $R_1$, can be a $C_1-C_2$ alkylenedioxy;

$R_3$ and $R_4$ are each independently selected from hydrogen, fluorine, chlorine, bromine, $C_1-C_3$ alkyl, hydroxy, $C_1-C_3$ alkoxy, nitro, amino, $C_1-C_3$ alkylamino, or $C_1-C_3$ dialkylamino, or together can be methylenedioxy; and $R_5$ is hydrogen, $C_3-C_5$ alkenyl, $C_1-C_3$ alkyl, or phenyl $C_1-C_3$ alkyl, and nontoxic, pharmaceutically acceptable addition salts thereof which have valuable pharmacological properties, particularly a long-lasting heart rate lowering effect and the effect of reducing the $O_2$ requirement of the heart.

38 Claims, No Drawings

AMINOTETRALIN DERIVATIVES

The present invention relates to new aminotetralin derivatives of formula I

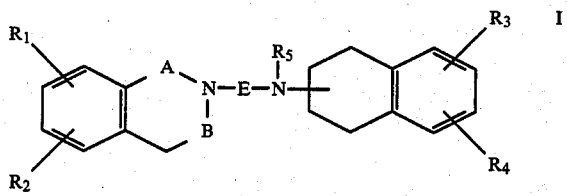

wherein

A is —CH$_2$—CH$_2$—, —CH=CH—, —NH—CO—,
   —CH$_2$—CO—, —CO—CO— or —CHOH—CO—;

B is methylene or, when A is —CH$_2$—CH$_2$—, —CH=CH—, —NH—CO— or —CH$_2$—CO—, B can also be carbonyl or thiocarbonyl;

E is a C$_2$-C$_4$ straight-chain alkylene, optionally substituted by a C$_1$-C$_3$ alkyl, or is 2-hydroxy-n-propylene, 2-hydroxy-n-butylene or 3-hydroxy-n-butylene;

R$_1$ is hydrogen, fluorine, chlorine, bromine, trifluoromethyl, nitro, amino, C$_1$-C$_3$ alkylamino, C$_1$-C$_3$ dialkylamino, C$_1$—C$_3$ alkyl, C$_1$-C$_3$ alkylthio, hydroxy, C$_1$-C$_3$ alkoxy or phenyl C$_1$-C$_3$ alkoxy;

R$_2$ is hydrogen, chlorine, bromine, hydroxy, C$_1$-C$_3$ alkoxy, phenyl C$_1$-C$_3$ alkoxy or C$_1$-C$_3$ alkyl or, together with R$_1$, can be a C$_1$-C$_3$ alkylenedioxy;

R$_3$ and R$_4$ are each independently selected from hydrogen, fluorine, chlorine, bromine, C$_1$-C$_3$ alkyl, hydroxy, C$_1$-C$_3$ alkoxy, nitro, amino, C$_1$-C$_3$ alkylamino or C$_1$-C$_3$ dialkylamino or together can be methylenedioxy; and R$_5$ is hydrogen, C$_3$-C$_5$ alkenyl, C$_1$-C$_3$ alkyl or phenyl C$_1$-C$_3$ alkyl, and nontoxic harmaceutically acceptable addition salts thereof.

Examples of the groups given above include the following.

R$_1$ can, for example, be hydrogen, fluorine, chlorine, bromine, methyl, ethyl, n-propyl, isopropyl, trifluoromethyl, hydroxy, methoxy, ethoxy, n-propoxy, isopropoxy, methylthio, ethylthio, isopropylthio, nitro, amino, methylamino, ethylamino, n-propylamino, isopropylamino, dimethylamino, diethylamino, di-n-propylamino, diisopropylamino, methyl-ethylamino, methyl-n-propylamino, methyl-isopropylamino, ethyl-n-propylamino, benzyloxy, 1-phenylethoxy, 1-phenylpropoxy, 2-phenylethoxy or 3-phenylpropoxy.

R$_2$ can, for example, be hydrogen, chlorine, bromine, methyl, ethyl, n-propyl, isopropyl, hydroxy, methoxy, ethoxy, n-propoxy, isopropoxy, benzyloxy, 1-phenylethoxy, 2-phenylethoxy, 2-phenylpropoxy or 3-phenylpropoxy or, together with R$_1$, can be methylenedioxy or ethylenedioxy.

R$_3$ and R$_4$ can each independently be selected from, for example, hydrogen, fluorine, chlorine, bromine, methyl, ethyl, n-propyl, isopropyl, hydroxy, methoxy, ethoxy, n-propoxy, isopropoxy, amino, methylamino, ethylamino, n-propylamino, isopropylamino, dimethylamino, diethylamino, di-n-propylamino, diisopropylamino or N-ethyl-methylamino.

R$_5$ can, for example, be hydrogen, methyl, ethyl, n-propyl, isopropyl, benzyl, 1-phenylethyl, 2-phenylethyl, 1-phenylpropyl, 1-methyl-1-phenylethyl, 3-phenylpropyl, allyl, n-but-2-enyl or n-pent-2-enyl.

E can, for example, be ethylene, n-propylene, n-butylene, 1-methylethylene, 2-ethyl-ethylene, 1-propyl-ethylene, 1-methyl-n-propylene, 2-methyl-n-propylene, 1-ethyl-n-propylene, 3-ethyl-n-propylene, 2-propyl-n-propylene, 2-methyl-n-butylene, 2-hydroxy-n-propylene, 2-hydroxy-n-butylene or 3-hydroxy-n-butylene.

In a subgeneric aspect, the invention provides compounds of formula Ia

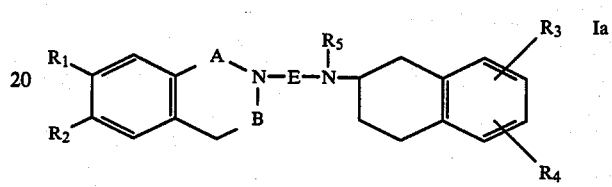

wherein

A is —CH$_2$—CH$_2$—, —CH=CH, —NH—CO—,
   —CH$_2$—CO—, —CO—CO— or —CHOH—CO—;

B is methylene or, when A is —CH$_2$—CH$_2$—or —CH=CH—, B can also be carbonyl or thiocarbonyl;

E is n-propylene;

R$_1$ is chlorine, bromine, methyl, methoxy, nitro, amino, methylamino or dimethylamino;

R$_2$ is chlorine, bromine, methyl or methoxy or can, together with R$_1$, be methylenedioxy or ethylenedioxy;

R$_3$ is hydrogen, chlorine, bromine, hydroxy, methoxy, amino, methylamino or dimethylamino;

R$_4$ is hydrogen, chlorine, or methoxy or can, together with R$_3$ be methylenedioxy; and R$_5$ is hydrogen, methyl or allyl, and nontoxic, pharmaceutically acceptable addition salts thereof.

A further subgeneric aspect of the invention includes compounds of general formula Ia wherein A is —CH$_2$CH$_2$— and B is carbonyl or thiocarbonyl, or A is —NH—CO— and B is methylene;

E is n-propylene;

R$_1$ and R$_2$ are each methoxy or together are methylenedioxy;

R$_3$ and R$_4$ are each methoxy or together are methylenedioxy; and

R$_5$ is hydrogen or methyl, and nontoxic, pharmaceutically acceptable addition salts thereof.

The new compounds have valuable pharmacological properties, particularly a long-lasting heart rate-lowering effect and the effect of reducing the O$_2$ requirement of the heart.

According to the invention the new compounds are obtained by the following processes:

(a) A compound of formula II

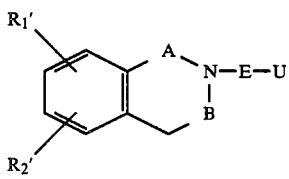

is reacted with a compound of formula III

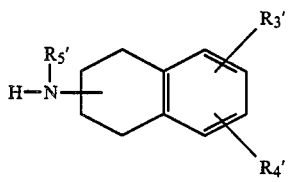

wherein

A, B and E are as hereinbefore defined, $R_1'$ is hydroxy, amino or alkylamino protected by a protecting group or has the meanings given for $R_1$ above;

$R_2'$ is hydroxy protected by a protecting group or has the meanings given for $R_2$ above;

$R_3'$ hydroxy, amino or alkylamino protected by a protecting group or has the meanings given for $R_3$ above;

$R_4'$ is hydroxy, amino or alkylamino protected by a protecting group or has the meanings given for $R_4$ above;

$R_5'$ is a protecting group for an amino or has the meanings given for $R_5$ above; and U is a nucleophilically exchangeable group such as halogen or sulphonyloxy (e.g. a chlorine, bromine or iodine, methanesulphonyloxy, p-toluenesulphonyloxy or ethoxysulphonyloxy). Any protecting group used is optionally subsequently split off.

The protecting group used for a hydroxy group can be, for example, trimethylsilyl, acetyl, benzoyl, benzyl or tetrahydropyranyl and the protecting group used for an amino or alkylamino can be, for example, acetyl, benzoyl, ethoxycarbonyl or benzyl.

The reaction is conveniently carried out in a solvent or mixture of solvents such as acetone, diethyl ether, methylformamide, dimethylformamide, dimethylsulphoxide, benzene, chlorobenzene, tetrahydrofuran, benzene/tetrahydrofuran, dioxan or in an excess of the compounds of general formulae II and/or III. It is optionally carried out in the presence of an acid-binding agent, e.g., an alkoxide such as potassium tert.butoxide, an alkali metal hydroxide such as sodium hydroxide or potassium hydroxide, an alkali metal carbonate such as potassium carbonate, an alkali metal amide such as sodamide, an alkali metal hydride such as sodium hydride, or a tertiary organic base such as triethylamine or pyridine, which latter can simultaneously also serve as the solvent, or a reaction accelerator such as potassium iodide, depending on the reactivity of the nucleophilically exchangeable group. Convenient temperatures are 0° to 150° C., preferably 50° to 120° C., e.g. at the boiling temperature of the solvent used. However, the reaction can also be carried out without a solvent. It is particularly advantageous to carry out the reaction in the presence of a tertiary organic base or an excess of the amine of general formula III which is being used.

The optional subsequent splitting off of a protecting group is preferably carried out by hydrolysis in an aqueous solvent, e.g. in water, isopranolol/water, tetrahydrofuran/water or dioxan/water, in the presence of an acid such as hydrochloric or sulphuric acid or in the presence of an alkali metal base such as sodium hydroxide or potassium hydroxide, at temperatures of 0° to 100° C., preferably at the boiling temprature of the reaction mixture. However, the splitting off of a benzyl group is preferably carried out by hydrogenolysis, e.g. with hydrogen in the presence of a catalyst such as palladium/charcoal in a solvent such as methanol, ethanol, ethyl acetate or glacial acetic acid, optionally with the addition of an acid such as hydrochloric acid at temperatures of 0° to 50° C., preferably at ambient temperature, under a hydrogen pressure of 1 to 7 bar, preferably 3 to 5 bar.

(b) Compounds of formula I wherein A is —CH$_2$—CH$_2$—, B is methylene or carbonyl and $R_5$ is not a $C_3$-$C_5$ alkenyl, can be prepared by hydrogenation of a compound of formula IV

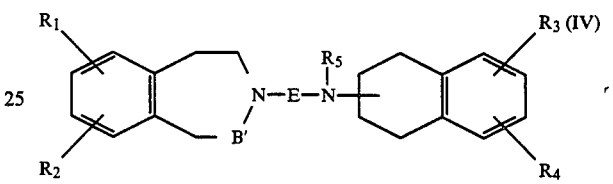

wherein $R_1$ to $R_5$ and E are as previously defined and

B' is methylene or carbonyl.

The hydrogenation is carried out in a solvent or mixture of solvents such as methanol, ethanol, ethyl acetate or glacial acetic acid with catalytically activated hydrogen, e.g. with hydrogen in the presence of platinum or palladium/charcoal, under a hydrogen pressure of 1 to 7 bar, preferably 3 to 5 bar, and at temperatures of 0° to 75° C., preferably 20° to 50° C.

If, in a compound of formula I, $R_5$ is alkenyl, this is simultaneously converted into the corresponding alkyl during the reduction or, if $R_1$ and/or $R_2$ is benzyloxy, this is converted into the corresponding hydroxy during the reaction.

(c) To prepare compounds of formula I wherein B is thiocarbonyl, a compound of formula V

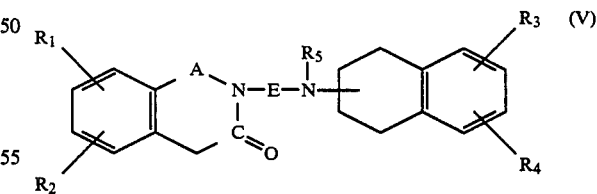

wherein $R_1$ and $R_5$, A and E are as previously defined is reacted with a sulphur-introducing agent.

The sulphur-introducing agent can be, for example, phosphorus pentasulphide or 2,4-bis(4-methoxyphenyl)-1,3-dithia-2,4-diphosphentan-2,4-disulphide, conveniently in a solvent such as toluene or xylene, at temperatures of 50° to 150° C., e.g. at the boiling temperature of the reaction mixture.

(d) To prepare compounds of formula I wherein A is CHOH—CO—, a compound of formula VI

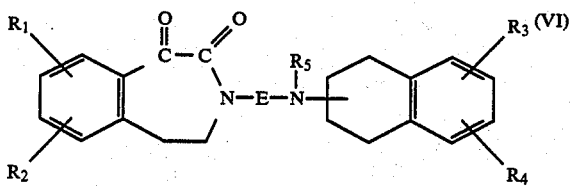

wherein $R_1$ to $R_5$ and E are as previously defined is reduced in the presence of a suitable reducing agent such as a metal hydride, e.g. sodium borohydride, in a suitable solvent such as water/methanol or methanol/ether, at temperatures of 0° to 80° C., preferably 15° to 40° C.

(e) To prepare compounds of formula I wherein A is —CH$_2$—CH$_2$— or —CH=CH— and B is methylene, a compound of formula VII

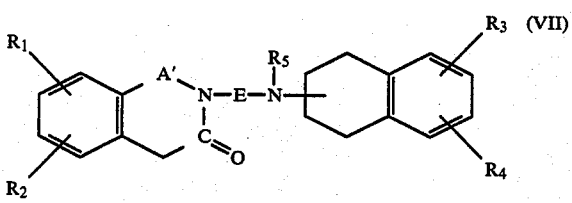

wherein $R_1$ to $R_5$ and E are as previously defined and A' is —CH$_2$—CH$_2$— or —CH=CH— is reduced a metal hydride such as lithium aluminum hydride or diborane or with a complex of borane and a thioether, e.g. with borane-dimethylsulphide complex, in a suitable solvent such as diethyl ether or tetrahydrofuran at temperatures of 0° to 50° C., preferably 10° to 25° C.

(f) To prepare compounds of formula I wherein A is —CO—CO—, a compound of formula VIII

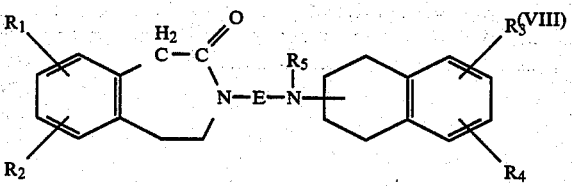

wherein $R_1$ to $R_5$ and E are as previously defined is oxidized with an oxidizing agent such as potassium permanganate, selenium dioxide or sodium dichromate in a suitable solvent or mixture of solvents such as water, water/dioxan, glacial acetic acid, water/acetic acid or acetic anhydride at temperatures of 0° to 100° C., preferably 20° to 80° C.

(g) To prepare comounds of formula I wherein A is —NH—CO— and E is a C$_2$-C$_4$ alkylene optionally substituted by a C$_1$-C$_3$ alkyl, a compound of formula IX

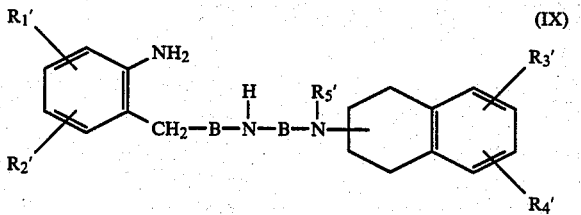

wherein
B and E are as previously defined;
$R_1'$ is hydroxy, amino or alkylamino protected by a protecting group or has the meanings previously given for $R_1$;
$R_2'$ is hydroxy, protected by a protecting group, or has the meanings previously given for $R_2$;
$R_3'$ and $R_4'$ are each independently hydroxy, amino or alkylamino, protected by a protecting group, or have the meanings previously given for $R_3$ and $R_4$;
$R_5'$ is a protecting group for an amino group or has the meanings previously given for $R_5$, with the exception of hydrogen, is reacted with a carbonic acid derivative of formula X $$W-CO-W' \qquad (X)$$

wherein W and W' are each independently a nucleophilically exchangeable group, e.g. chlorine or bromine, C$_1$-C$_3$ alkoxy, imidazol-1-yl or trichloromethoxy, when the other of W and W' is chlorine or bromine, and any protecting group used is optionally subsequently split off.

A suitable protecting group for a hydroxy can be, for example, trimethylsilyl, acetyl, benzoyl, benzyl or tetrahydropyranyl and a suitable protecting group for an amino or alkylamino can be acetyl, benzoyl, ethoxycarbonyl or benzyl.

The reaction is conveniently carried out in a solvent or mixture of solvents such as ethyl acetate, methylene chloride, carbon tetrachloride, benzene, tetrahydrofuran, benzene/tetrahydrofuran, dioxan or acetonitrile, conveniently at temperatures of 0° to 150° C., preferably at the boiling temperature of the solvent used, e.g. 40° to 100° C., and optionally in the presence of an acid-binding agent such as potassium carbonate, sodium hydroxide, potassium hydroxide, pyridine or triethylamine, while the latter can simultaneously also serve as solvent. However, the reaction can also be carried out without a solvent. If, in a compound of formula X, at least one of W and W' is a C$_1$-C$_3$ alkoxy the reaction is preferably carried out in an excess of the ester used as solvent.

The optional subsequent splitting off of any protecting group used is preferably carried out by hydrolysis in an aqueous solvent, e.g. in water, isopropanol/water, tetrahydrofuran/water or dioxan/water, in the presence of an acid such as hydrochloric or sulphuric acid or in the presence of an alkali metal base such as sodium hydroxide or potassium hydroxide at temperatures of 0° to 100° C., preferably at the boiling temperature of the reaction mixture. However, the splitting off of a benzyl group can also be carried out by hydrogenolysis, e.g. with hydrogen in the presence of a catalyst such as palladium/charcoal, in a solvent such as methanol, ethanol, ethyl acetate or glacial acetic acid, optionally with the addition of an acid such as hydrochloric acid at temperatures of 0° to 50° C., but preferably at ambient temperature, under a hydrogen pressure of 1 to 7 bar, preferably 3 to 5 bar.

(h) In another embodiment, a compound of formula XI

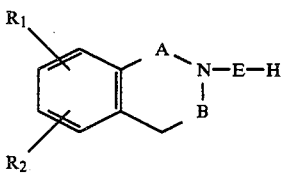

(XI)

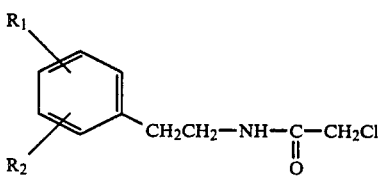

(XIV)

wherein A, B, E, $R_1$ and $R_2$ are as previously defined, except that in E two hydrogen atoms of a —CH$_2$ or —CH$_3$ are replaced by an oxygen atom, is reacted with a compound of formula XII

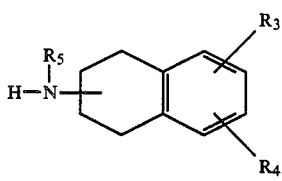

(XII)

wherein $R_3$ to $R_5$ are as previously defined, in the presence of a reducing agent.

The reaction is appropriately carried out in a suitable solvent or mixture of solvents such as methanol, ethanol, ethanol/ethyl acetate or dioxan at temperatures of 0° to 100° C. preferably 20° to 80° C.

It is particularly advantageous to carry out the reductive amination in the presence of a complex metal hydride such as lithium cyanoborohydride or sodium cyanoborohydride, preferably at a pH of 6 to 7 and at ambient temperature or, in order to prepare compounds of formula I wherein $R_5$ is hydrogen, in the presence of palladium/charcoal under a hydrogen pressure of 5 bar. Any benzyl groups which may be present can simultaneously be split off by hydrogenolysis and/or any double bonds can be hydrogenated.

The compounds of formula I so-obtained can also be converted into the addition salts thereof, particularly their nontoxic, pharmaceutically acceptable addition salts with inorganic or organic acids. Suitable acids include, for example, hydrochloric, hydrobromic, sulphuric, phosphoric, acetic, lactic, citric, tartaric, succinic, maleic or fumaric acid.

The compounds of formulae II to XII used as starting materials are known from the literature in some cases or can be obtained by processes known per se.

Thus, for example, a starting compound of formula II is obtained by reacting a corresponding benzazepine with a corresponding halogen compound and optionally by subsequent reaction with a corresponding amine. The benzazepine unsubstituted in the 3 position which is required for this is obtained by cyclizing a corresponding compound e.g. by cyclizing a compound of formula XIII

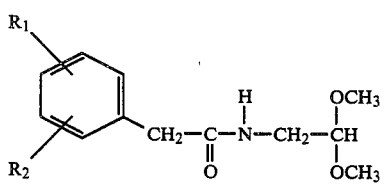

(XIII)

or of formula XIV with optional subsequent catalytic hydrogenation and/or reduction of the carbonyl group, e.g. with sodium borohydride/glacial acetic acid (see EP-AI No. 0,007,070) and/or oxidation, e.g. with selenium dioxide.

A compound of formulae IV to VIII used as starting material is preferably obtained by reacting a corresponding halogen compound with a suitable amine and optionally subsequently splitting off any protecting groups used to protect the hydroxy and/or amino groups.

A compound of formula IX used as starting material is obtained, for example, by reduction of a corresponding nitro compound.

A compound of formulae III or XII is obtained, for example, by reacting a corresponding tetralone with a corresponding amine with subsequent reduction.

A compound of formula XI is obtained, for example, by reacting a corresponding benzazepine unsubstituted in the 3 position with a corresponding haloacetal or haloketal with subsequent hydrolysis.

As previously mentioned, the new compounds of formula I and the nontoxic, pharmaceutically acceptable addition salts thereof have valuable pharmacological properties, particularly a long-lasting effect of lowering heart rate and reducing the $O_2$ requirement of the heart, with only slight central side effects.

For example, the following compounds:

A=1-[7,8-Dimethoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane hydrochloride;

B=1-[7,8-Dimethoxy-1,3,4,5-tetrahydro-2H-3-benzazepin-2-on-3-yl]-3-[N-(6,7-dimethoxy-1,2,3,4-tetrahydronaphth-2-yl)-amino]-propane hydrochloride;

C=1-7,8-Dimethoxy-1,3,4,5-tetrahydro-2H-3-benzazepin-2-on-3-yl]-3-[N-methyl-N-(7-methoxy-1,2,3,4-tetrahydronaphth-2-yl)-amino]-propane hydrochloride; and D=1-[7,8-Dimethoxy-1,3,4,5-tetrahydro-2H-3-benzazepin-2-on-3-yl]-3-[N-methyl-N-(6-methoxy-1,2,3,4-tetrahydronaphth-2-yl)-amino]-propane hydrochloride are tested for their biological properties as follows.

Effect on heart rate in rats

The effect of the test substances on heart rate is tested in rats (two) with an average weight of from 250 to 300 g for each dose. The rats are anesthetized with pentobarbital (50 mg/kg i.p. and 20 mg/kg s.c.). The test substances are injected in aqueous solution into the jugular vein (0.1 ml/100 g).

The blood pressure is measured using a canula tied into a carotid artery and heart rate was recorded from an ECG (II or III derivation) obtained with needle electrodes. The heart rate of the animals in the control period is between 350 and 400 beats per minute (b/min).

The table 1 shows the results obtained:

TABLE 1

| Substance | Dosage (mg/kg) | Lowering of heart rate measured 20 minutes after administration of substance (b/min) |
|---|---|---|
| A | 5.0 | −176 |
| B | 5.0 | −203 |
| C | 5.0 | −184 |
| D | 5.0 | −165 |

Effect on heart rate in cats

The effect of the test substances on heart rate is tested on cats (seven) of both sexes with an average weight of from 2.5 to 3.5 kg for each dose. The cats are anesthetised with chloralose (80 mg/kg). The test substance is injected in aqueous solution into the vena saphena.

The heart rate is recorded before and after administration of the substance using a Grass tachograph from the electrocardiogram (electrode attached to the chest wall) on a Grass polygraph.

Table 2 shows the results obtained:

TABLE 2

| Substance | Dosage (mg/kg) | Lowering of heart rate | Half life (minutes) |
|---|---|---|---|
| A | 0.3 i.v. | −30% | >120 |
| A | 1.0 i.v. | −58% | >120 |
| B | 1.0 i.v. | −55% | >120 |

The compounds prepared according to the invention have no toxic side effects in therapeutic doses. Thus, for example, substances A and B administered intravenously, even in a high dosage of 20 mg/kg in mice, show no toxic side effects apart from slight sedation. In view of their pharmacological properties the compounds according to the invention are suitable for the treatment of sinus tachycardia of various origins and for the prophylaxis and therapy of ischaemic heart diseases.

The dosage required in order to achieve such an effect is appropriately 0.03 to 0.4 mg/kg of body weight, preferably 0.07 to 0.25 mg/kg of body, once or twice a day. The compounds of formula I prepared accordind to the invention and the nontoxic, pharmaceutically acceptable addition salts thereof with inorganic or organic acids, optionally together with other active substances, can be processed with one or more inert conventional carriers and/or diluents, e.g. with corn starch, lactose, cane sugar, microcrystalline cellulose, magnesium stearate, polyvinyl pyrrolidone, citric acid, tartaric acid, water, water/ethanol, water/glycerol, water/sorbitol, water/polyethylene glycol, propylene glycol, carboxymethylcellulose or fatty substances such as hard fat or suitable mixtures thereof, to form preparations such as plain or coated tablets, capsules, powders, suspensions, drops, ampoules, syrups or suppositories.

The following Examples illustrate the invention:

Preparation of the starting compounds

EXAMPLE A 7,8-Dimethoxy-1,3-dihydro-2H-3-benzazepin-2-one (a) 3,4-Dimethoxy-phenylacetyl chloride Over a period of two hours, thionyl chloride (600 ml) is added dropwise, with stirring, to a suspension of 3,4-dimethoxy-phenylacetic acid (549.4 g) in methylene chloride (600 ml). After the development of gas has ended (16 hours) the mixture is refluxed for a further hour. After the highly volatile components have been removed the residue is distilled in vacuo. Yield: 486 g. Bp: 134°–136° C./1.95 mbar.

(b) N-(2,2-Dimethoxyethyl)-3,4-dimethoxy-phenylacetamide

While cooling with ice, a solution of 3,4-dimethoxy-phenylacetyl chloride (485.2 g) in methylene chloride (1.1 liters) is added dropwise at 15°–20° C. to a solution of aminoacetaldehyde dimethyl acetal (246.2 ml) and triethylamine (315 ml) in methylene chloride (2.2 liters) and the mixture is stirred for one hour at 16°–18° C. It is then extracted several times with water, dried over magnesium sulphate and concentrated by evaporation. The oil obtained slowly crystallizes out. Yield: 608 g. Mp: 66°–69° C.

(c) 7,8-Dimethoxy-1,3-dihydro-2H-3-benzazepin-2-one

A solution of N-(2,2-dimethoxyethyl)-3,4-dimethoxy-phenylacetamide (600.6 g) in concentrated hydrochloric acid (3 liters) is mixed with glacial acetic acid (3 liters). After it has been left to stand for 17 hours at ambient temperature the mixture is poured onto ice. The crystals precipitated are suction filtered, washed with water until neutral and then dried. Yield: 350 g. Mp: 234°–237° C.

EXAMPLE B 7,8-Dimethoxy-1,3,4,5-tetrahydro-2H-3-benzazepin-2-one

A suspension of 7,8-dimethoxy-1,3-dihydro-2H-3-benzazepin-2-one (21.9 g, 0.1 mol) and 10% palladium/charcoal (1.5 g) in glacial acetic acid (200 ml) is hydrogenated at 50° C. under hydrogen pressure (5 bar). After the catalyst has been filtered off the solvent is evaporated off in vacuo and the residue is taken up in methylene chloride. After extraction with sodium bicarbonate solution and washing with water, the mixture is dried over magnesium sulphate and concentrated and purified over silica gel with methylene chloride and then with increasing amounts of methanol (up to 10%). Yield: 12.6 g. Mp: 188°–191° C.

EXAMPLE C 7,8-Dimethoxy-2,3,4,5-tetrahydro-1H-3-benzazepine

A solution of glacial acetic acid (1.8 g) in dioxan (10 ml) is added to a suspension of 7,8-dimethoxy-1,3,4,5-tetrahydro-2-H-3-benzazepin-2-one (1.3 g, 6 mmol) and sodium borohydride (1.1 g, 3 mmol) in dioxan (20 ml). The resulting mixture is refluxed for 3 hours, evaporated and mixed with water. The mixture is extracted twice with methylene chloride, the extract is concentrated by evaporation and the residue is taken up in ether. After filtering, the ether is eliminated in vacuo. Yield: 1.1 g. Mp: 86°–89° C.

EXAMPLE D 6,9-Dimethoxy-1,3-dihydro-2H-3-benzazepin-2-one

N-(2,2-dimethoxyethyl)-2,5-dimethoxyphenyl-acetamide (2.0 g, 0.007 mol) has polyphosphoric acid (3 ml) poured over it and the resulting mixture is stirred for 60 minutes at 90° C. Then ice water is added, the product precipitated is suction filtered and dried. Yield: 0.98 g. Mp: 188°–191° C.

EXAMPLE E

7,8-Dimethyl-1,3-dihydro-2H-3-benzazepin-2-one

The title compound is prepared analogously to Example D from N-(2,2-dimethoxyethyl)-3,4-dimethylphenylacetamide and polyphosphoric acid. Mp: 220°–224° C.

EXAMPLE F

7,8-Dimethoxy-1,3,4,5-tetrahydro-2H-3-benzazepin-2,4-dione (a) 7,8-Dimethoxy-2-amino-4-bromo-1H-3-benzazepine hydrobromide First 3,4-dimethoxy-o-phenylene-diacetonitrile (3.7 g, 0.017 mol) is suspended in glacial acetic acid (10 ml) and 30% hydrobromic acid in glacial acetic acid (12 ml) is added at 20° C. Then, the mixture is stirred for 3 hours at ambient temperature. The precipitate obtained is suction filtered, washed with glacial acetic acid and then with acetone/ether and dried. Yield: 5.3 g. Mp: 210°–211° C. (Decomp.)

(b) 7,8-Dimethoxy-1,3,4,5-tetrahydro-2H-3-benzazepin-2,4-dione

First, 7,8-dimethoxy-2-amino-4-bromo-1H-3-benzazepine hydrobromide (5.3 g, 0.014 mol) is dissolved in 100 ml of water at 85° C., then 1.3 g of anhydrous sodium acetate is added and the mixture is heated to 90° C. for one hour. The reaction mixture is cooled, suction filtered, washed with cold water and dried. Yield: 2.9 g. Mp: 235° C. (Decomp.)

EXAMPLE G

7,8-Dimethoxy-2,3,-dihydro-1H-3-benzazepine

A boiling suspension of lithium aluminum hydride (0.8 g) in absolute dioxan (100 ml) is mixed with 7,8-dimethoxy-1,3-dihydro-2H-3-benzazepin-2-one (2.2 g, 0.01 mol) and then refluxed for 3 hours. While cooling with iced water, 10% ammonium chloride solution is added and the precipitate formed is suction filtered. The filtrate is concentrated (to about 20 ml) in vacuo, the white precipitate obtained is suction filtered and washed with a little dioxan. Yield: 0.9 g. Mp: 162°–163° C.

EXAMPLE H

1-(7,8-Dimethoxy-1,3,4,5-tetrahydro-2H-3-benzazepin-2-on-3-yl)-3-chloropropane (a) 1-(7,8-Dimethoxy-1,3 dihydro-2H-3-benzazepin-2-on-3-yl)-3-chloropropane First, 7,8-dimethoxy-1,3-dihydro-2H-3-benzazepin-2-one (131.5 g, 0.6 mol) is suspended in dimethylsulphoxide (900 ml) and potassium tert. butoxide (80.8 g, 0.72 mol) is added with stirring. After 10 minutes the resulting solution is added dropwise, while cooling with ice water, to 1-bromo-3-chloropropane (77 ml, 0.72 mol) in dimethylsulphoxide (300 ml).

After one hour it is poured onto ice water. After a short time the greasy precipitate begins to crystallize. The precipitate is suction filtered, dissolved in acetone, reprecipitated with water, suction filtered and dried. Yield: 155.5 g. Mp: 101°–103° C.

(b) 1,(7,8-Dimethoxy-1,3,4,5-tetrahydro-2H-3-benzazepin-2-on-3-yl)-3-chloropropane First, 1-(7,8-dimethoxy-1,3-dihydro-2H-3-benzazepin-2-on-3-yl)-3-chloropropane (59.2 g, 0.2 mol) is hydrogenated in glacial acetic acid (500 ml) in the presence of 10% palladium/charcoal (5 g) for 6 hours at 50° C. and at 5 bar. The catalyst is suction filtered, the glacial acetic acid is distilled off in vacuo and the residue is neutralized with potassium carbonate after the addition of water. The precipitate is suction filtered, washed with water to remove salts and dried. Yield: 53 g. Mp: 85°–86° C.

EXAMPLE I

1-(7,-Bromo-8-methoxy-1,3,4,5-tetrahydro-2H-3-benzazepin-2-on-3-yl)-3-chloropropane (a) 8-Methoxy-1,3,4,5-tetrahydro-2H-3-benzazepin-2-one First, 8-methoxy-1,3-dihydro-2H-3-benzazepin-2-one (56.8 g, 0.3 mol) (Mp: 190°–191° C.), dissolved in glacial acetic acid (600 ml), is hydrogenated in the presence of 10% palladium/charcoal (5 g) at 80° C. and at 5 bar for 12 hours. The catalyst is suction filtered and the acetic acid is distilled off in vacuo. The residue is mixed with water, neutralized with potassium carbonate, the precipitate obtained is suction filtered, washed with water and dried. Yield: 51.1 g. Mp: 160°–161° C.

(b) 7-Bromo- and 8-bromo-8-methoxy-1,3,4,5-tetrahydro-2H-3-benzazepin-2-one

At 3°–5° C. bromine (6.4 g=2.03 ml, 0.04 mol) in glacial acetic acid (10 ml) is added dropwise, with stirring, to 8-methoxy-1,3,4,5-tetrahydro-2H-3-benzazepin-2-one (7.4 g, 0.04 mol) in 80% acetic acid (100 ml). After 15 minutes the mixture is poured onto ice water and neturalized with potassium carbonate, the precipitate is suction filtered, washed with a little water and dried. The mixture of isomers obtained is separated by chromatography over a column of silica gel (eluant: ethyl acetate).

Yield: 5.7 g of 9-bromo isomer.

IR spectrum (methylene chloride): 3400 cm$^{-1}$ (NH), 1660 cm$^{-1}$(C=O).

4.1 g of 7-bromo isomer.

IR spectrum (potassium bromide): 3220 cm$^{-1}$ (NH), 1665 cm$^{-1}$ (C=O).

(c) 1-(7-Bromo-8-methoxy-1,3,4,5-tetrahydro-2H-3-benzazepin-2-on-3-yl)-3-chloropropane First, 55% sodium hydride dispersion in oil (0.24 g, 5.5 mmol) is added to 7-bromo-8-methoxy-1,3,4,5-tetrahydro-2H-3-benzazepine-2-one (1.35 g, 5 mmol) in dimethylsulphoxide (15 ml) and the mixture is stirred for 10 minutes at 35°–40° C. The solution is added dropwise to 1-bromo-3-chloropropane (0.79 g, 5.5 mmol) in dimethylsulphoxide (5 ml), with stirring. Then the mixture is stirred for 2 hours at ambient temperature, poured onto ice water and extracted four times with methylene chloride. The methylene chloride extracts are washed several times with water, dried and concentrated in vacuo.

The residue is purified over a silica gel column with ethyl acetate as eluant. Yield: 210 mg Mp: 119°–120° C.

EXAMPLE J

1-(7-Methoxy-1,3,4,5-tetrahydro-2H-3-benzazepin-2-on-3-yl)-3-chloropropane (a)

(7-Methoxy-1,3,4,5-tetrahydro-2H-3-benzazepin-2-one

N-chloroacetyl-N-[2-(3-methoxy-phenyl)-ethyl]amine (3.1 g, 0.0136 mol) is dissolved in ethanol (270 ml) and water (1530 ml) and illuminated for 10 hours in a nitrogen atmosphere at 20°–25° C. with a high pressure mercury lamp. The solution is evaporated down (about 400 ml), mixed with sodium bicarbonate and extracted several times with ethyl acetate. The extracts are dried over magnesium sulphate, concentrated by evaporation and the residue is purified over a silica gel column with ethyl acetate as eluant. Yield: 820 mg. Mp: 152°–154° C.

(b)

1-(7-Methoxy-1,3,4,5-tetrahydro-2H-3-benzazepin-2-on-3-yl)-3-chloropropane

First, 7-methoxy-1,3,4,5-tetrahydro-2H-3-benzazepin-2-one (1.15 g, 6 mmol) is dissolved in absolute tetramethylurea (30 ml), mixed with 55% sodium hydride dispersion in oil (300 mg) and stirred for 2 hours at 20°–25° C. under a nitrogen atmosphere. The resulting reaction mixture is added dropwise, with stirring, at 15°–20° C. under a nitrogen atmosphere to 1-chloro-3-iodopropane (1.6 g, 7.8 mmol) dissolved in tetramethylurea (20 ml) and stirred for 3 hours at ambient temperature. Then, ethyl acetate (300 ml) are added and the mixture is extracted six times with water. The organic solution is dried over magnesium sulphate, concentrated by evaporation and the residue is purified oer a silica gel column with methylene chloride and increasing amounts of ethanol (up to 2%). Yield: 410 mg. IR spectrum (methylene chloride): 1650 cm$^{-1}$ (C=O).

EXAMPLE K

1-(7-Nitro-8-methoxy-1,3,4,5-tetrahydro-2H-3-benzazepin-2-on-3-yl)-3-chloropropane First, 1-(8-methoxy-1,3,4,5-tetrahydro-2H-3-benzazepin-2-on-3-yl)-3-chloropropane (28.5 g, 0.016 mol) is stirred into concentrated nitric acid (350 ml) for half an hour at 20°–25° C. The solution is then poured onto ice water, neutralized with potassium carbonate and extracted twice with methylene chloride. The extract is dried over magnesium sulphate, concentrated by evaporation in vacuo and the residue is purified over a silica gel column with ethyl acetate as eluant. Yield: 11 g. Mp: 127°–128° C.

EXAMPLE L

2-Methylamino-6,7-dimethoxy-1,2,3,4-tetrahydronaphthalene (a) 6,7-Dimethoxy-1,2,3,4-tetrahydronaphthalen-2-one, sodium hydrogensulphite adduct First, 3,4-dimethoxyphenylacetyl chloride (49.2 g, 0.229 mol) is dissolved in methylene chloride (500 ml) and added dropwise to a suspension of aluminium chloride (123 g, 0.923 mol) in methylene chloride (3800 ml) at −5° C. After ethylene has been introduced for 1 hour the mixture is mixed with ice water and extracted with 2N hydrochloric acid and with saturated sodium hydrogen carbonate solution. The organic phase is dried over magnesium sulphate, concentrated by evaporation and mixed with saturated sodium hydrogensulphite solution. Yield: 28.2 g. Mp: from 160° C. (decomp.).

(b)

2-Methylamino-6,7-dimethoxy-1,2,3,4-tetrahydronaphthalene hydrochloride

Next, 6,7-dimethoxy-1,2,3,4-tetrahydronaphthalen-2-one (92.8 g, 0.45 mol) is mixed, under a current of nitrogen, as a partial suspension in absolute ethanol (1125 ml), with acetic acid (77.1 ml, 1.35 mol) and 3 A molecular sieve (112.5 g). After methylamine (42.5 g, 1.35 mol) has been introduced at ambient temperature the solution is decanted off from the molecular sieve, platinum (IV) oxide (4.64 g) is added and the mixture is hydrogenated for 40 minutes at ambient temperature under a hydrogen pressure (5 bar). After the catalyst has been filtered off the solvent is evaporated in vacuo (500 ml) and the hydrochloride is precipitated with ethereal hydrochloric acid. Yield: 7.2 g. Mp: 256°–258° C.

EXAMPLE M

2-Benzylamino-6,7-dimethoxy-1,2,3,4-tetrahydronaphthalene

The title compound is prepared analogously to Example L by reacting 6,7-dimethoxy-1,2,3,4-tetrahydronaphthalen-2-one with benzylamine. Mp: 237°–238° C.

EXAMPLE N

5,6-Dimethoxy-2-methylamino-1,2,3,4-tetrahydronaphthalene (a) 5,6-Dimethoxy-1,2,3,4-tetrahydronaphthalen-2-one, sodium hydrogensulphite adduct Sodium (16.4 g, 0.715 mol) is added in batches, with stirring, within 45 minutes, to 2,5,6-trimethoxynaphthalene (12 g, 0.055 mol) in absolute ethanol (220 ml). To complete the reaction the mixture is then refluxed for a further hour. After cooling in an ice bath, the sodium chloride precipitate is suction filtered and washed with methylene chloride. The filtrate is stirred for a short time after the addition of further methylene chloride, the organic phase is separated and the aqueous-acidic solution is again extracted with methylene chloride. The organic solutions are combined, washed once with water, dried over magnesium sulphate and concentrated by evaporation. The residue is mixed with a solution of sodium hydrogensulphite (25 g) in water and (80 ml) and ethanol (20 ml). Yield: 12.5 g.

(b)

5,6-Dimethoxy-2-methylamino-1,2,3,4-tetrahydronaphthalene hydrochloride

The title compound is prepared analogously to Example L. Mp: 203°–204° C.

The following compounds were prepared analogously to Example N:

2-Methylamino-1,2,3,4-tetrahydronaphthalene hydrochloride. Mp: 180°–181° C.

5-Methoxy-2-methylamino-1,2,3,4-tetrahydronaphthalene hydrochloride. Mp: 205°–206° C.

7-Methoxy-2-methylamino-1,2,3,4-tetrahydronaphthalene hydrochloride. Mp: 216°–219° C.

6-Methoxy-2-methylamino-1,2,3,4-tetrahydronaphthalene hydrochloride. Mp: 167°–168° C.

8-Methoxy-2-methylamino-1,2,3,4-tetrahydronaphthalene hydrochloride. Mp: 145°–146° C.

EXAMPLE O

2-Amino-5-methoxy-1,2,3,4-tetrahydronaphthalene

First, 5-methoxy-1,2,3,4-tetrahydronaphthalen-2-one (17.6 g, 0.1 mol) is dissolved in methanol (800 ml) and 1,2-dichloroethane (200 ml), then it is mixed with ammonium acetate (77 g) and sodium cyanoborohydride (5.4 g) and stirred for 2 days at laboratory temperature. The reaction mixture is adjusted to pH 2 with concentrated hydrochloric acid and the solvent is distilled off in vacuo. The residue is dissolved in ethyl acetate/water. The aqueous phase is separated off, made alkaline with 50% sodium hydroxide solution with cooling and extracted twice with methylene chloride. The extract is dried, treated with Fuller's earth/activated charcoal and concentrated by evaporation. The residue is dissolved in acetone and the hydrochloride is precipitated with ethereal hydrochloric acid. Yield: 2 g. Mp: 260°–262° C. (decomp.).

EXAMPLE P 3-(7,8-Dimethoxy-1,3-dihydro-2H-3-benzazepin-2-on-3-yl)-propionaldehyde (a)

3-(7,8-Dimethoxy-1,3-dihydro-2H-3-benzazepin-2-on-3-yl)-propionaldehyde diethyl acetal This is prepared analogously to Example H (a) by reacting 7,8-dimethoxy-1,3-dihydro-2H-3-benzazepin-2-one with 3-chloro-propionaldehyde diethyl acetal.

(b)

3-(7,8-Dimethoxy-1,3-dihydro-2H-3-benzazepin-2-on-3-yl)-propionaldehyde

First, 3-(7,8-Dimethoxy-1,3-dihydro-2H-3-benzazepin-2-on-3-yl)-propionaldehyde diethyl acetal (3.5 g, 0.01 mol) is heated in 2N sulphuric acid (50 ml) and ethanol (50 ml) to 40° C. for 2 hours. The alcohol is then distilled off in vacuo, the residue is made alkaline with saturated potassium carbonate solution with cooling and extracted several times with ethyl acetate. The ethyl acetate extract is extracted twice with sodium hydrogensulphite solution. The bisulphite extract is acidified with concentrated hydrochloric acid and heated for half an hour to 40° C. in vacuo in order to eliminate the sulphur dioxide. Then, saturated potassium carbonate solution is added and the mixture is extracted several times with methylene chloride, dried over magnesium sulphate and evaporated. Yield: 1.7 g. Mp: 95°–96° C.

EXAMPLE Q

1-Amino-3-[N-methyl-N-(7-methoxy-1,2,3,4-tetrahydronaphth-2-yl)-amino]-propane (a)

2-[N-Methyl-N-(2-cyano-ethyl)-amino]-7-methoxy-1,2,3,4-tetrahydronaphthalene

First, 7-methoxy-2-methylamino-1,2,3,4-tetrahydronaphthalene (5.76 g, 0.0253 mol) is dissolved in methanol (100 ml) with stirring. Acrylonitrile (2.07 ml, 0.0316 mol) is added and the mixture is heated for 3 hours to 50°–55° C. Then the solvent is distilled off. Yield: 6.2 g. $R_f$ value: 0.75 (alumina, eluant: methylene chloride).

(b)

1-Amino-3-[N-methyl-N-(7-methoxy-1,2,3,4-tetrahydronaphth-2-yl)-amino]-propane

First, 2-[N-methyl-N-(2-cyano-ethyl)-amino]-7-methoxy-1,2,3,4-tetrahydronaphthalene (6.7 g, 0.0274 mol) is dissolved in methanol (80 ml) saturated with ammonia at 20° C., then Raney nickel (0.8 g) is added and the mixture is hydrogenated at 50° C. under hydrogen pressure (5 bar) for 3 hours. The catalyst is filtered off and the filtrate is evaporated by rotary evaporation. Yield: 5.4 g. $R_f$ value: 0.25 (alumina, eluant: 95 parts by volume of methylene chloride + 5 parts by volume of ethanol).

The following compound is prepared analogously to Example Q:

1-Amino-3-[N-methyl-N-(6,7-dimethoxy-1,2,3,4-tetrahydronaphth-2-yl)-amino]-propane. $R_f$ value: 0.27 (alumina, eluant: 95 parts by volume of methylene chloride + 5 parts by volume of ethanol).

EXAMPLE R

1-[2-(2-Amino-4,5-dichlorophenyl)-ethylamino]-3-[N-methyl-N-(6,7-dimethoxy-1,2,3,4-tetrahydronaphth-2-yl)-amino]-propane (a) 3,4-Dichlorophenylacetic acid First, 3,4-dichloro-benzylcyanide (65.1 g, 0.35 mol) is refluxed for 2 hours in 2M sodium hydroxide solution (700 ml), then it is mixed with activated charcoal and filtered. The filtrate is acidified with concentrated hydrochloric acid while being cooled with ice water, the precipitate obtained is suction filtered, washed with water until neutral and dried. Yield: 71 g. Mp: 82°–84° C.

(b) 4,5-Dichloro-2-nitro-phenylacetic acid

Here, 3,4-dichlorophenylacetic acid (66.7 g, 0.325 mol) is added in batches, with stirring at 5° C., to a mixture of fuming nitric acid (600 ml) and concentrated nitric acid (300 ml). The mixture is stirred for one hour while cooling is continued and the solution is allowed to rise to 20° C. over a period of a further 1.5 hours. The reaction mixture is poured onto ice, the precipitate is suction filtered, washed with ice water until neutral and then dried. Yield: 54.2 g. Mp: 119°–120° C.

(c)

1-[2-(4,5-Dichloro-2-nitro-phenyl)-1-oxo-ethylamino]-3-[N-methyl-N-(6,7-dimethoxy-1,2,3,4-tetrahydronaphth-2-yl)-amino]-propane Here, 3,4-dichloro-2-nitro-phenylacetic acid (10 g, 0.04 mol) is suspended in absolute ethyl acetate (150 ml) and at ambient temperature N,N'-carbonyldiimidazole (8.1 g, 0.05 mol) is added with stirring. The precipitate initially obtained is dissolved after 3 hours. A solution of 1-amino-3-[N-methyl-N-(6,7-dimethoxy-1,2,3,4-tetrahydronaphth-2-yl)-amino]-propane (11.1 g, 0.04 mol) in absolute ethyl acetate (150 ml) is added dropwise to this solution. The resulting reacting mixture is stirred for a further 2 hours at 20° C. and left to stand overnight. It is extracted twice with 2M sodium hydroxide solution and once with water, dried over magnesium sulphate and the solvent is distilled off in vacuo. The residue is purified by column chromatography over alumina N (900 g) (activity II, eluant: methylene chloride + 1% ethanol). Yield: 18.2 g. IR spectrum (methylene chloride): 1670 cm$^{-1}$ (C=O).

(d)

1-[2-(2-Amino-4,5-dichlorophenyl)-1-oxo-ethylamino]-3-[N-methyl-N-(6,7-dimethoxy-1,2,3,4-tetrahydronaphth-2-yl)-amino]-propane Here, 1-[2-(4,5-dichloro-2-nitro-phenyl)-1-oxo-ethylamino]-3-[N-methyl-N-(6,7-dimethoxy-1,2,3,4-tetrahydronaphth-2-yl)-amino]-propane (15.8 g, 0.031 mol) is dissolved in methanol (300 ml) and mixed with 98% hydrazine hydrate (4.65 ml). Raney nickel (2 g) is added in batches with stirring. Then the mixture is stirred for 2 hours at ambient temperature, the catalyst is filtered off and the filtrate is concentrated by evaporation in vacuo. The viscous residue is purified by column chromatography over alumina N (400 g) [activity II, eluant: methylene chloride and increasing amounts of ethanol (up to 1%)]. Yield: 13.9 g. IR spectrum (methylene chloride): 1660 cm$^{-1}$ (C=O), 1515 cm$^{-1}$ (Amide-II).

(e)

1-[2-(2-Amino-4,5-dichlorophenyl)-ethylamino]-3-[N-methyl-N-(6,7-dimethoxy-1,2,3,4-tetrahydronaphth-2-yl)-amino]-propane Next, 1-[2-(2-amino-4,5-dichlorophenyl)-1-oxo-ethylamino]-3-[N-methyl-N-(6,7-dimethoxy-1,2,3,4-tetrahydronaphth-2-yl)-amino]-propane (4.8 g, 0.01 mol) is dissolved in absolute tetrahydrofuran (100 ml) and mixed with boron trifluoride-diethyl ether complex (1.25 g, 1.1 ml). Then, a 10M toluene solution of borane-dimethylsulphide complex (1.6 ml) diluted with absolute tetrahydrofuran (20 ml) is added to the reaction mixture with stirring, under a nitrogen atmosphere and with heating to reflux temperature, and the resulting mixture is refluxed for a further 8 hours. The solvent is distilled off in vacuo, the residue is heated in 6M hydrochloric acid (100 ml) to 80° C. for one hour, cooled and extracted twice with ethyl acetate. The hydrochloric acid solution is then made alkaline with 50% sodium hydroxide solution while cooling with ice water and extracted several times with methylene chloride. The extract is dried over magnesium sulphate, concentrated by evaporation in vacuo and the residue is purified by column chromatography over alumina N (170 g) [activity II, eluant: methylene chloride and increasing amounts of ethanol (up to 5%)]. Yield: 1 g.

EXAMPLE S

1-[2-(2-Amino-4,5-dimethoxyphenyl)-ethylamino]-3-[N-methyl-N-(6,7-dimethoxy-1,2,3,4-tetrahydronaphth-2-yl)-amino]-propane (a) 4,5-Dimethoxy-2-nitro-phenylacetic acid First, 3,4-dimethoxyphenylacetic acid (49.05 g, 0.25 mol) is added in batches to concentrated nitric acid (500 ml), with cooling, at 30° C. and stirred for a further 15 minutes with cooling. The reaction mixture is poured onto ice water (1.5 liters), the precipitate obtained is suction filtered, washed with ice water until neutral and dried. Yield: 56.4 g. Mp: 209°–211° C.

(b)

1-[2-(4,5-Dimethoxy-2-nitro-phenyl)-1-oxo-ethylamino]-3-[N-methyl-N-(6,7-dimethoxy-1,2,3,4-tetrahydronaphth-2-yl)-amino]-propane The title compound of this paragraph is prepared from 4,5-dimethoxy-2-nitrophenylacetic acid (5.25 g, 0.0217 mol) and of 1-amino-3-[N-methyl-N-(6,7-dimethoxy-1,2,3,4-tetrahydronaphth-2-yl)-amino]-propane (6.04 g, 0.0218 mol) analogously to Example R(c). Yield: 8.6 g. R$_f$ value: 0.8 (alumina, eluant: 95 parts by volume of methylene chloride+5 parts by volume of ethanol).

(c)

1-[2-(2-Amino-4,5-dimethoxyphenyl)-1-oxo-ethylamino]-3-[N-methyl-N-(6,7-dimethoxy-1,2,3,4-tetrahydronaphth-2-yl)-amino]-propane Here, 1-[2-(4,5-dimethoxy-2-nitro-phenyl)-1-oxo-ethylamino]-3-[N-methyl-N-(6,7-dimethoxy-1,2,3,4-tetrahydronaphth-2 yl)-amino]-propane (8.5 g, 0.017 mol) is dissolved in methanol (100 ml), mixed with 10% palladium on charcoal (9.8 g) and hydrogenated for one hour at 20° C. under hydrogen pressure (5 bar). The catalyst is filtered off and the filtrate is concentrated by rotary evaporation. Yield: 7.8 g. R$_f$ value: 0.2 (alumina, eluant: 98 parts by volume of methylene chloride+2 parts by volume of ethanol).

(d)

1-[2-(2-Amino-4,5-dimethoxy-phenyl)-ethylamino]-3-[N-methyl-N-(6,7-dimethoxy-1,2,3,4,-tetrahydronaphth-2-yl)-amino]-propane The title compound of this paragraph is prepared from 1-[2-(2-amino-4,5-dimethoxyphenyl)-1-oxo-ethylamino]-3-[N-methyl-N-(6,7-dimethoxy-1,2,3,4,-tetrahydronaphth-2-yl)-amino]-propane (7.8 g, 0.0165 mol) analogously to Example R(e). Yield: 2.7 g R$_f$ value: 0.2 (alumina, eluant: 95 parts by volume of methylene chloride+5 parts by volume of ethanol).

EXAMPLE T

1-[2-(2-Amino-4,5-dimethoxyphenyl)-ethylamino]-3-[N-methyl-N-(7-methoxy-1,2,3,4-tetrahydronaphth-2-yl)-amino]-propane (a) 4,5-Dimethoxy-2-nitro-phenylacetic acid The title compound here is prepared from 3,4-dimethoxy phenylacetic acid (49.05 g, 0.25 mol) analogously to Example S(a). Yield: 56.4 g. Mp: 209°–211° C.

(b)

1-[2-(4,5-Dimethoxy-2-nitro-phenyl)-1-oxo-ethylamino]-3-[N-methyl-N-(7-methoxy-1,2,3,4-tetrahydronaphth-2-yl)-amino]-propane The title compound here is prepared from 4,5-dimethoxy-2-nitrophenylacetic acid (5.25 g, 0.0217 mol) and 1-amino-3-[N-methyl-N-(7-methoxy-1,2,3,4-tetrahydronaphth-2-yl)-amino]-propane (5.4 g, 0.0217 mol) analogously to Example R(c). Yield: 8.2 g Mp: 116°–118° C.

(c)

1-[2-(2-Amino-4,5-dimethoxyphenyl)-1-oxo-ethylamino]-3-[N-methyl-N-(7-methoxy-1,2,3,4-tetrahydronaphth-2-yl)-amino]-propane The title compound here is prepared from 1-[2-(4,5-dimethoxy-2-nitro-phenyl)-1-oxo-ethylamino]-3-[N-methyl-N-(7-methoxy-1,2,3,4-tetrahydro-naphth-2-yl)-amino]-propane (8.2 g, 0.0174 mol) analogously to Example S(c). Yield: 7.4 g. R$_f$ value: 0.2 (alumina, eluant: 98 parts by volume of methylene chloride+2 parts by volume of ethanol).

(d)

1-[2-(2-Amino-4,5-dimethoxy-phenyl)-ethylamino]-3-[N-methyl-N-(7-methoxy-1,2,3,4-tetrahydronaphth-2-yl)-amino]-propane The title compound here is prepared from 1-[2(-2-amino-4,5-dimethoxyphenyl)-1-oxo-ethylamino]-3-[N-methyl-N-(7-methoxy-1,2,3,4-tetrahydronaphth-2-yl)-amino]-propane (6.73 g, 0.0153 mol) analogously to Example R(e). Yield: 4.2 g. $R_f$ value: 0.2 (alumina, eluant: 95 parts by volume of methylene chloride+5 parts by volume of ethanol).

Preparation of the end products

EXAMPLE 1

1-[7,8-Dimethoxy-1,3-dihydro-2H-3-benzazepin-2-on-3-yl]-3-[N-methyl-N-(6,7-dimethoxy-1,2,3,4,-tetrahydronaphth-2-yl)-amino]-propane A mixture of 2-methylamino-6,7-dimethoxy-1,2,3,4-tetrahydronaphthalene (1.72 g, 0.0078 mol), triethylamine (1.09 ml, 0.0078 mol) and 1-(7,8-dimethoxy-1,3-dihydro-2H-3-benzazepin-2-on-3-yl)-3-chloropropane (2.3 g, 0.0078 mol) is heated to a reaction temperature of 90° C. in steps within one hour and kept at this temperature for 2 hours. The initial suspension slowly changes into a clear solution and begins to precipitate in a jelly-like manner after about 30 minutes. The cooled reaction mixture is dissolved in 0.5M sodium hydroxide solution/ethyl acetate, the organic phase is washed with water, dried over magnesium sulphate, concentrated by evaporation in vacuo and purified over alumina (300 g), neutral, activity II, with methylene chloride and then with increasing quantities of ethanol (up to 20%). The hydrochloride is precipitated from a solution in acetone using ethereal hydrochloric acid. Yield: 1.39 g Mp: >125° C. (Decomp.).

EXAMPLE 2

1-[7,8-Dimethoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane The title compound is prepared analogously to Example 1 by reacting 2-methylamino-6,7-dimethoxy-1,2,3,4-tetrahydronaphthalene with 1-(7,8-dimethoxy-1,3,4,5-tetrahydro-2H-3-benzazepin-2-on-3-yl)-3-chloro-propane. Mp: 236°–238° C.

EXAMPLE 3

1-[7,8-Dimethoxy-1,3,4,5-tetrahydro-2H-3-benzazepin-2-on-3-yl]-3-[N-benzyl-N-(6,7-dimethoxy-1,2,3,4-tetrahydronaphth-2-yl)-amino]-propane The title compound is prepared analogously to Example 1 by reacting 2-benzylamino-6,7-dimethoxy-1,2,3,4-tetrahydronaphthalene with 1-(7,8-dimethoxy-1,3,4,5-tetra hydro-2H-3-benzazepin-2-on-3-yl)-3-chloropropane. IR spectrum (methylene chloride): 1645 cm$^{-1}$ (C=O).

EXAMPLE 4

1-[7,8-Dimethoxy-1,3,4,5-tetrahydro-2H-3-benzazepin-2-on-3-yl]-3-[N-(6,7-dimethoxy-1,2,3,4-tetrahydronaphth-2-yl)-amino]-propane Here, 1-[7,8-dimethoxy-1,3,4,5-tetrahydro-2H-3-benzazepin-2-on-3-yl]-3-[N-benzyl-N-(6,7-dimethoxy-1,2,3,4-tetrahydronaphth-2-yl)-amino]-propane (0.78 g, 0.0014 mol) is hydrogenated in glacial acetic acid (20 ml) in the presence of 10% palladium/charcoal (0.1 g) for 3 hours at ambient temperature under pressure (5 bar). The catalyst is removed by suction filtering, the glacial acetic acid is distilled off in vacuo, the residue is taken up in methylene chloride/saturated potassium carbonate solution, the organic phase is washed with water, dried over magnesium sulphate, evaporated again and purified over alumina (100 g), neutral, activity II, with methylene chloride and then with increasing amounts of ethanol (up to 40%). The hydrochloride is precipitated from a solution in acetone with ethereal hydrochloric acid. Yield: 0.45 g Mp: 222°–223° C.

EXAMPLE 5

1-[7,8-Dimethoxy-1,3,4,5-tetrahydro-2H-3-benzazepin-2-on-3-yl][N-methyl-N-(1,2,3,4-tetrahydronaphth-2-yl)-amino]-propane The title compound is prepared analogously to Example 1 by reacting 1-(7,8-dimethoxy-1,3,4,5-tetrahydro-2H-3-benzazepin-2-on-3-yl)-3-chloropropane, triethylamine and 2-methylamino-1,2,3,4-tetrahydronaphthalene. Mp: 140°–142° C. (decomp.).

EXAMPLE 6

1-[7,8-Dimethoxy-1,3,4,5-tetrahydro-2H-3-benzazepin-2-on-3-yl]-3-[N-methyl-N-(5-methoxy-1,2,3,4-tetrahydronaphth-2-yl)-amino]-propane The title compound is prepared analogously to Example 1 by reacting 1-(7,8-dimethoxy-1,3,4,5-tetrahydro-2H-3-benzazepin-2-on-3-yl)-3-chloropropane, triethylamine and 5-methoxy-2-methylamino-1,2,3,4-tetrahydronaphthalene. Mp: 149°–150° C. (decomp.).

EXAMPLE 7

1-[7,8-Dimethoxy-1,3,4,5-tetrahydro-2H-3-benzazepin-2-on-3-yl]-3-[N-methyl-N-(7-methoxy-1,2,3,4-tetrahydronaphth-2-yl)-amino]-propane The title compound is prepared analogously to Example 1 by reacting 1-(7,8-dimethoxy-1,3,4,5-tetrahydro-2H-3-benzazepin-2-on-3-yl)-3-chloropropane, triethylamine and 7-methoxy-2-methylamino-1,2,3,4-tetrahydronaphthalene. Mp: 189°–190° C. (decomp.).

EXAMPLE 8

1-[7,8-Dimethoxy-1,3,4,5-tetrahydro-2H-3-benzazepin-2-on-3-yl]-3-[N-methyl-N-(6-methoxy-1,2,3,4-tetrahydronaphth-2-yl)-amino]-propane The title compound is prepared analogously to Example 1 by reacting 1-(7,8-dimethoxy-1,3,4,5-tetrahydro-2H-3-benzazepin-2-on-3-yl)-3-chloropropane, triethylamine and 6-methoxy-2-methylamino-1,2,3,4-tetrahydronaphthalene. Mp: 122°–123° C. (decomp.).

EXAMPLE 9

1-[7,8-Dimethoxy-1,3,4,5-tetrahydro-2H-3-benzazepin-2-on-3-yl]-3-[N-methyl-N-(8-methoxy-1,2,3,4-tetrahydronaphth-2-yl)-amino]-propane The title compound is prepared analogously to Example 1 by reacting 1-(7,8-dimethoxy-1,3,4,5-tetrahydro-2H-3-benzazepin-2-on-3-yl)-3-chloropropane, triethylamine and 8-methoxy-2-methylamino-1,2,3,4-tetrahydronaphthalene. Mp: 141°–143° C. (decomp.).

EXAMPLE 10

1-[7,8-Dimethoxy-1,3,4,5-tetrahydro-2H-3-benzazepin-2-on-3-yl]-3-[N-methyl-N-(5,6-dimethoxy-1,2,3,4-tetrahydronaphth-2-yl)-amino]-propane The title compound is prepared analogously to Example 1 by reacting 1-(7,8-dimethoxy-1,3,4,5-tetrahydro-2H-3-benzazepin-2-on-3-yl)-3-chloropropane, triethylamine and 5,6-dimethoxy-2-methyl-amino-1,2,3,4-tetrahydronaphthalene. Mp: 216°–217° C. (decomp.).

EXAMPLE 11

1-[7,8-Dimethoxy-1,3,4,5-tetrahydro-2H-3-benzazepin-2-on-3-yl]-3-[N-(1,2,3,4-tetrahydronaphth-2-yl)-amino]-propane Here, 3-[7,8-dimethoxy-1,3-dihydro-2H-3-benzazepin-2-on-3-yl]-propionaldehyde (1.5 g, 0.0054 mol) and 2-amino-1,2,3,4-tetrahydronaphthalene (0.8 g, 0.0054 mol) are hydrogenated in ethanol (150 ml) in the presence of 10% palladium/charcoal (0.5 g) for 15 hours under pressure (5 bar) at 60° C. The catalyst is removed by suction filtering, the filtrate is concentrated in vacuo and the residue is purified over silica gel by column chromatography with methylene chloride and increasing amounts of ethanol (up to 4%). The clean fractions are concentrated by evaporation and the hydrochloride is precipitated from acetone. Yield: 1.35 g. Mp: 229°–230° C.

EXAMPLE 12

1-[7,8-Dimethoxy-1,3,4,5-tetrahydro-2H-3-benzazepin-2-on-3-yl]-3-[N-methyl-N-(5-methoxy-1,2,3,4-tetrahydronaphth-2-yl)-amino]-propane The title compound is prepared analogously to Example 11 by reacting 3-(7,8-dimethoxy-1,3-dihydro-2H-3-benzazepin-2-on-3-yl)-propionaldehyde and 2-amino-5-methoxy-1,2,3,4,-tetrahydronaphthalene. Mp: 190° C.

EXAMPLE 13

1-[7,8-Dimethoxy-2,3,4,5-tetrahydro-1H-3-benzazepin-3-yl]-3-[N-methyl-N-(6,7-dimethoxy-1,2,3,4-tetrahydronaphth-2-yl)-amino]-propane Here, 1-[7,8-dimethoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane hydrochloride (1.4 g, 0.0027 mol) is added to a suspension of lithium aluminum hydride (0.24 g, 0.0062 mol) in diethyl ether (50 ml) and refluxed for 7 hours. Then water and 15% sodium hydroxide solution are added, the mixture is concentrated in vacuo and purified over silica gel (50 g) (32–63 μm) with methylene chloride and increasing amounts of ethanol (up to 15%) as eluant. Yield: 0.6 g. Mp: 92°–93° C.

EXAMPLE 14

1-[7,8-Dimethoxy-1,3,4,5-tetrahydro-2H-3-benzazepin-1,2-dion-3-yl]-3-[N-methyl-N-(6,7-dimethoxy-1,2,3,4-tetrahydronaphth-2-yl)-amino]-propane Here, 1-[7,8-dimethoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane (1.64 g, 0.0034 mol) is added at 70° C. to a suspension of selenium dioxide (0.41 g, 0.0036 mol) and Celite (0.34 g) in 1,4-dioxan (17 ml) and water (0.68 ml) is added and the mixture is refluxed for 40 hours. After cooling, it is suction filtered, concentrated by rotary evaporation in vacuo and purified over silica gel (40 g) (32–63 μm) with methylene chloride and increasing amounts of ethanol (up to 40%). The clean fractions are concentrated by evaporation and the hydrochloride is precipitated from acetone. Yield: 0.6 g. Mp: >145° C. (decomp.).

EXAMPLE 15

1-[7,8-Dimethoxy-1,3,4,5-tetrahydro-2H-3-benzazepin-2-thion-3-yl]-3-[N-methyl-N-(6,7-dimethoxy-1,2,3,4-tetrahydronaphth-2-yl)-amino]-propane Here, 1-[7,8-dimethoxy-1,3,4,5-tetrahydro-2H-3-benzazepin-2-on-3-yl]-3-[N-methyl-N-(6,7-dimethoxy-1,2,3,4-tetrah hydro-naphth-2-yl)-amino]-propane and 2,4-bis-(4-methoxyphenyl)-1,3-dithia-2,4-diphosphetan-2,4-disulphide (1.21 g, 0.003 mol) are refluxed for 2 hours in toluene (12 ml). After evaporation in vacuo, the residue is purified over neutral alumina (240 g) with an activity of II–III with methylene chloride and increasing quantities of ethanol (up to 2%). Yield: 1.4 g. Mp: 70°–75° C.

EXAMPLE 16

1-[7,8-Dimethoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane Here, 1-[7,8-dimethoxy-1,3-dihydro-2H-3-benzazepin-2-on-3-yl]-3-[N-methyl-N-(6,7-dimethoxy-1,2,3,4-tetrahydronaphth-2-yl)-amino]-propane (1.6 g, 0.0033 mol) is hydrogenated in glacial acetic acid (20 ml) in the presence of 10% palladium/charcoal (50 g) for 6 hours at 50° C. and at pressure (5 bar). The catalyst is removed by suction filtering, the glacial acetic acid is distilled off in vacuo and the residue is neutralized after the addition of water and potssium carbonate. The precipitate is suction filtered, washed with water to remove any salts and dried. The hydrochloride is precipitated from a solution in acetone using ethereal hydrohcloric acid. Yield: 1.2 g. Mp: 236°–238° C.

EXAMPLE 17

1-[1-Hydroxy-7,8-dimethoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane Here, 1-[7,8-dimethoxy-1,3,4,5-tetrahydro-2H-3-benzazepin-1,2-dion-3-yl]-3-[N-methyl-N-(6,7-dimethoxy-1,2,3,4-tetrahydronaphth-2-yl)-amino]-propane (0.70 g 0.0014 mol) is dissolved in a mixture of methanol/water=(95:5, 21 ml) then sodium borohydride (0.060 g, 0.0016 mol) is added and the mixture is stirred for 20 minutes at ambient temperature. It is then acidified with hydrochloric acid (2 mol/l), made alkaline with methanolic ammonia and extracted with methylene chloride, dried over magnesium sulphate, concentrated by evaporation and the residue is purified over a column [alumina N (50 g), activity II, eluant: methylene chloride and then with increasing amounts of ethanol (up to 3%)]. The residue is dissolved in acetone and mixed with ethereal hydrochloric acid. The precipitate obtained is suction filtered, washed with ether and dried. Yield: 0.18 g. Mp: 141°–143° C.

EXAMPLE 18

1-[7,8-Dimethoxy-1,3,4,5-tetrahydro-2H-1,3-benzodiazepin-2-on-3-yl]-3-[N-methyl-N-(7-methoxy-1,2,3,4-tetrahydronapht-2-yl)-amino]-propane Here, 1-[2-(2-amino-4,5-dimethoxy-phenyl)-ethyl amino]-3-[N-methyl-N-(7-methoxy-1,2,3,4-tetrahydro naphth 2-yl)-amino]-propane (2.0 g, 0.005 mol) and N,N'-carbonyldiimidazole (1 g, 0.006 mol) are reflxed for 60 minutes in absolute ethyl acetate (40 ml). After extraction with saturated potassium carbonate solution and with water, the product which has been evaporated in vacuo is dissolved in methylene chloride and precipitated with petroleum ether. yield: 1.2 g. Mp: 163°–165° C.

EXAMPLE 19

1-[7,8-Dichloro-1,3,4,5-tetrahydro-2H-1,3-benzodiazepin-2-on-3-yl]-3-[N-methyl-N-(6,7-dimethoxy-1,2,3,4-tetrahydronaphth-2-yl)-amino]-propane (a)
1-[2-(2-Amino-4,5-dichlorophenyl)-N-carbonylimidazolyl-ethylamino]-3-[N-methyl-N-(6,7-dimethoxy-1,2,3,4-tetrahydronaphth-2-yl)-amino]-propane Here, 1-[2-(2-amino-4,5-dichlorophenyl)-ethylamino]-3-[N-methyl-N-(6,7-dimethoxy-1,2,3,4-tetra hydronaphth-2-yl)-amino]-propane (1 g, 0.0021 mol) is dissolved in absolute ethyl acetate (50 ml), mixed with N,N'-carbonyldiimidazole (0.42 g, 0.0026 mol) and refluxed for one hour under a nitrogen atmosphere. The mixture is cooled, extracted twice with 2N sodium hydroxide solution and twice with water, dried over magnesium sulphate and concentrated by evaporation in vacuo. The residue is purified by column chromatography alumina N, (80 g) activity II, eluant: methylene chloride and increasing amounts of ethanol (up to 3%)]. For further purification the product is dissolved in methylene chloride and precipitated with petroluem ether. Yield: 480 mg. Mp: 178° C.

(b)
1-[7,8-Dichloro-1,3,4,5-tetrahydro-2H-1,3-benzodiazepin-2-on-3-yl]-3-[N-methyl-N-(6,7-dimethoxy-1,2,3,4-tetrahydronaphth-2-yl)-amino]-propane Here, 1-[2-(2-amino-4,5-dichlorophenyl)-N-carbonylimidazolylethylamino]-3-[N-methyl-N-(6,7-dimethoxy-1,2,3,4-tetrahydronaphth-2-yl)-amino]-propane (0.3 g, 0.61 ml) is refluxed for 3 hours in tetramethylurea (10 ml) and ethyldiisopropylamine (10 ml). Ethyldiisopropylamine is distilled off in vacuo, the residue is taken up in ethyl acetate, extracted several times with water, dried over magnesium sulphate and concentrated with water, dried over magnesium sulphate and concentrated by evaporation in vacuo. The residue is dissolved in a little methylene chloride and precipitated with petroleum ether. Yield: 190 mg. Mp: 195°–197° C.

EXAMPLE 20

1-[7,8-Dimethoxy-1,3,4,5-tetrahydro-2H-1,3-benzodiazepin-2-on-3-yl]-3-[N-methyl-N-(6,7-dimethoxy-1,2,3,4-tetrahydronaphth-2-yl)-amino]-propane The title compound is prepared from 1-[2-(2-amino-4,5-dimethoxy-phenyl)-ethylamino]-3-[N-methyl-N-(6,7-dimethoxy-1,2,3,4-tetrahydronaphth-2-yl)-amino]-propane and N,N'-carbonyldiimidazole analogously to Example 18. Mp: 187°–188° C.

Elemental Analysis—Calculated: C,67.06; H,7.71; N,8.69. Found: C,66.91; H,7.83; N,8.61.

EXAMPLE 21

1-[7,8-Dimethoxy-1,3-dihydro-2H-3-benzazepin-3-yl]-3-[N-methyl-N-(6,7-dimethoxy-1,2,3,4-tetrahydronaphth-2-yl)-amino]-propane The title compound is prepared from 1-[7,8-dimethoxy-1,3-dihydro-2H-3-benzazepin-2-on-3-yl]-3-[N-methyl-N-(6,7-dimethoxy-1,2,3,4-tetrahydronaphth-2-yl)-amino]-propane and lithium aluminum hydride analogously to Example 13. Mp: 115°–116° C.

Elemental Analysis—Calculated: C,72.07; H,8.21; N,6.00. Found: C,71.80; H,8.10; N,5.88.

EXAMPLE 22

1-[7,8-Dimethoxy-1,3,4,5-tetrahydro-2H-3-benzazepin-2-on-3-yl]-3-[N-allyl-N-(6,7-dimethoxy-1,2,3,4-tetrahydronaphth-2-yl)-amino]-propane The title compound is prepared from 1-[7,8-dimethoxy-1,3,4,5-tetrahydro-2H-3-benzazepin-2-on-3-yl]-3-chloropropane and 2-allylamino-6,7-dimethoxy-1,2,3,4-tetrahydronaphthalene analogously to Example 1. Mp: 226°–228° C.

Elemental Analysis—Calculated C,66.10; H,7.58; Cl,6.50; N,5.14. Found: C,65.89; H,7.44; Cl,6.54; N,5.25.

EXAMPLE 23

1-[7,8-Ethylenedioxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane The title compound is prepared from 1-[7,8-ethylenedioxy-1,3,4,5-tetrahydro-2H-3-benzazepin-2-on-3-yl]-3-chloropropane and 6,7-dimethoxy-2-methylamino-1,2,3,4-tetrahydronaphthalene analogously to Example 1. Mp: 152°–157° C.

Elemental Analysis—Calculated: C,65.04; H,7.21, Cl 6.86; N,5.42. Found: C,64.81; H,7.15, Cl 6.94; N,5.40.

EXAMPLE 24

1-[7,8-Methylenedioxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane The title compound is prepared from 1-[7,8-methylenedioxy-1,3,4,5-tetrahydro-2H-3-benzazepin-2-on-3-yl]-3-chloropropane and 6,7-dimethoxy-2-methylamino-1,2,3,4-tetrahydronaphthalene analogously to Example 1. Mp: 158° C. (decomp.).

Elemental Analysis—Calculated: C,64.67; H,7.01; Cl,7.05; N,5.57. Found: C,65.50; H,7.16; Cl,7.14; N,5.91.

EXAMPLE 25

1-[7,8-Dimethoxy-1,3,4,5-tetrahydro-2H-3-benzazepin-2-on-3-yl]-3-[N-methyl-N-(6,7-dichloro-1,2,3,4-tetrahydronaphth-2-yl)-amino]-propane The title compound is prepared from 1-[7,8-dimethoxy-1,3,4,5-tetrahydro-2H-3-benzazepin-2-on-3-yl]-3-chloropropane and 6,7-dichloro-2-methylamino-1,2,3,4-tetrahydronaphthalene analogously to Example 1. Mp.: 130° C.

Elemental Analysis—Calculated: C,59.15; H,6.30; Cl,20.15; N,5.31. Found: C,58.37; H,6.56; Cl,20.38; N,5.28.

EXAMPLE 26

1-[7,8-Dimethoxy-1,3,4,5-tetrahydro-2H-3-benzazepin-2-on-3-yl]-3-[N-methyl-N-(6,7-methylenedioxy-1,2,3,4-tetrahydro-naphth-2-yl)-amino]-propane The title compound is prepared from 1-[7,8-dimethoxy-1,3,4,5-tetrahydro-2H-3-benzazepin-2-on-3-yl]-3-chloropropane and 2-methylamino-6,7-methylenedioxy-1,2,3,4-tetra-hydronaphthalene analogously to Example 1. Mp: >148° C. (decomp.).

Elemental Analysis—Calculated: C,64.47; H,7.01; Cl,7.05; N,5.57. Found: C,64.50; H,7.39; Cl,7.02; N,5.22.

The following compounds are obtained analogously to the preceding Examples:

1-[7,8-methylenedioxy-1,3,4,5-tetrahydro-2H-3-benzazepin-2-on-3-yl]-3-[N-methyl-N-(6,7-methylenedioxy-1,2,3,4-tetrahydronaphth-2-yl)-amino]-propane;

1-[7-bromo-8-methoxy-1,3,4,5-tetrahydro-2H-3-benzazepin-2-on-3-yl]-3-[N-methyl-N-(6,7-methylenedioxy-1,2,3,4-tetrahydronaphth-2-yl)-amino]-propane;

1-[7-chloro-8-methoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane;

1-[7-nitro-8-methoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane;

1-[7-amino-8-methoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane; and 1-[7,8-dimethoxy-1,3,4,5-tetrahydro-2H-1,3-benzodiazepin-2-on-3-yl]-3-[N-methyl-N-(6-methoxy-1,2,3,4-tetrahydronaphth-2-yl)-amino]-propane

EXAMPLE I

Tablets containing 1-[7,8-dimethoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane hydrochloride

| Composition: | |
|---|---|
| 1 tablet contains | |
| Active substance | 10.0 mg |
| Corn starch | 57.0 mg |
| Lactose | 48.0 mg |
| Polyvinyl pyrrolidone | 4.0 mg |
| Magnesium stearate | 1.0 mg |
| | 120.0 mg |

Method

The active substance, corn starch, lactose and polyvinyl pyrrolidone are mixed together and moistened with water. The moist mixture is pressed through a screen (1.5 mm mesh) and then dried (45° C.). The dry granulate is passed through a screen (1.0 mm mesh) and mixed with magnesium stearate. The finished mixture is compressed in a tablet press using punches (7 mm diameter) which are provided with a dividing slot, in order to form tablets.

EXAMPLE II

Coated tablets containing 1-[7,8-dimethoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane hydrochloride

| Composition: | |
|---|---|
| 1 tablet core contains | |
| Active substance | 5.0 mg |
| Corn starch | 41.5 mg |
| Lactose | 30.0 mg |
| Polyvinyl pyrrolidone | 3.0 mg |
| Magnesium stearate | 0.5 mg |
| | 80.0 mg |

Method

The active substance, corn starch, lactose and polyvinyl pyrrolidone are thoroughly mixed and moistened with water. The moist mass is pressed through a screen (1 mm mesh), dried at about 45° C. and then the granulate is passed through a screen again.

After the magnesium stearate has been added, convex tablet cores (6 mm diameter) are pressed out in a tablet-making machine. The tablet cores thus produced are covered in known manner with a coating consisting essentially of sugar and talc. The finished coated tablets are polished with wax. Weight of tablet: 130 mg.

EXAMPLE III

Ampoules containing 1-[7,8-dimethoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane hydrochloride

| 1 ampoule contains: | |
|---|---|
| Active substance | 5.0 mg |
| Sorbitol | 50.0 mg |
| Water for injection ad | 2.0 mg |

Method

The active substance is dissolved in water for injection in a suitable vessel and the solution is made isotonic with sorbitol.

After filtering through a membrane filter the solution is decanted into cleaned sterilized ampules under a current of nitrogen and heated in an autoclave for 20 minutes in a current of water vapor.

EXAMPLE IV

Suppositories containing 1-[7,8-dimethoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane hydrochloride

| 1 suppository contains: | |
|---|---|
| Active substance | 0.015 g |
| Hard fat (e.g. Witepsol H19 and W45) | 1.685 g |
| | 1.700 g |

Method

The hard fat is melted. At 38° C. the ground active substance is homogeneously dispersed in the melt. It is cooled to 35° C. and poured into slightly chilled suppository moulds.

EXAMPLE V

Drops solution containing 1-[7,8-dimethoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane hydrochloride

| 100 ml of solution contains: | |
|---|---|
| Active substance | 0.010 g |
| Hydroxyethyl cellulose | 0.15 g |
| Tartaric acid | 0.10 g |
| Sorbitol solution containing 70% dry matter | 30.0 g |
| Glycerol | 10.0 g |
| Benzoic acid | 0.15 g |
| Distilled water ad | 100 ml |

Method

The distilled water is heated to 70° C. Hydroxyethyl cellulose, benzoic acid and tartaric acid are dissolved therein with stirring. The mixture is cooled to ambient temperature and the glycerol and sorbitol solution are added with stirring. The active ingredient is added at ambient temperature and stirred until completely dissolved. The solution is then evacuated in order to eliminate air from the liquid, with stirring.

What is claimed is:

1. A compound having the formula

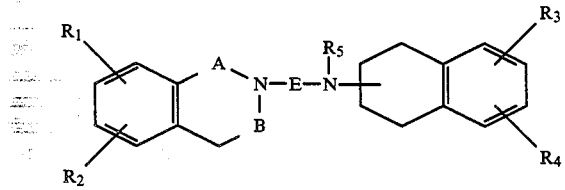

wherein

A is $-CH_2-CH_2-$, $-CH=CH-$, $-NH-CO-$, or $-CH_2-CO-$, $-CO-CO-$ or $-CHOH-CO-$;

B is methylene or, when A is $-CH_2-CH_2-$, $-CH=CH-$, $-NH-CO-$ or $-CH_2-CO-$, B can also be carbonyl or thiocarbonyl;

E is a $C_2-C_4$ straight-chain alkylene, optionally substituted by a $C_1-C_3$ alkyl, or is 2-hydroxy-n-propylene, 2-hydroxy-n-butylene or 3-hydroxy-n-butylene;

$R_1$ is hydrogen, fluorine, chlorine, bromine trifluoromethyl, nitro, amino, $C_1-C_3$ alkylamino, $C_1-C_3$ dialkylamino, $C_1-C_3$ alkyl, $C_1-C_3$ alkylthio, hydroxy, $C_1-C_3$ alkoxy or phenyl $C_1-C_3$ alkoxy;

$R_2$ is hydrogen, chlorine, bromine, hydroxy, $C_1-C_3$ alkoxy, phenyl $C_1-C_3$ alkoxy or $C_1-C_3$ alkyl or, together with $R_1$, can be a $C_1-C_2$ alkylenedioxy;

$R_3$ and $R_4$ are each independently selected from hydrogen, fluorine, chlorine, bromine, $C_1-C_3$ alkyl, hydroxy, $C_1-C_3$ alkoxy, nitro, amino, $C_1-C_2$ alkylamino or $C_1-C_3$ dialkylamino or together can be methylenedioxy;

$R_5$ is hydrogen, $C_3-C_5$ alkenyl, $C_1-C_3$ alkyl or phenyl $C_1-C_3$ alkyl and nontoxic, pharmaceutically acceptable addition salts thereof.

2. A compound of claim 1 having the formula

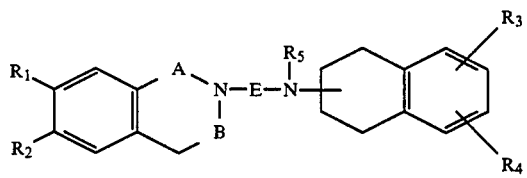

wherein

A is $-CH_2-CH_2-$, $-CH=CH-$, $-NH-CO-$, $-CH_2-CO-$, $-CO-CO-$ or $-CHOH-CO-$;

B is methylene or, when A is $-CH_2-CH_2-$ or $-CH=CH-$, can also be carbonyl or thiocarbonyl;

E is n-propylene;

$R_1$ is chlorine, bromine, methyl, methoxy, nitro, amino, methylamino or dimethylamino;

$R_2$ is chlorine, bromine, methyl or methoxy or can, together with $R_1$, can be methylenedioxy or ethylenedioxy;

$R_3$ is hydrogen, chlorine, bromine, hydroxy, methoxy, amino, methylamino or dimethylamino;

$R_4$ is hydrogen, chlorine, or methoxy or, together with $R_3$, can be methylenedioxy; and $R_5$ is hydrogen, methyl or allyl, and nontoxic, pharmaceutically acceptable addition salts thereof.

3. A compound of claim 2 wherein

A is $-CH_2CH_2-$ and B is carbonyl or thiocarbonyl or

A is $-NH-CO-$ and B is methylene;

E is n-propylene;

$R_1$ and $R_2$ are each methoxy or together are methylenedioxy;

$R_3$ and $R_4$ are each methoxy or together are methylenedioxy; and $R_5$ is hydrogen or methyl, and nontoxic, pharmaceutically acceptable addition salts thereof.

4. A compound of claim 1 which is 1-[7,8-dimethoxy-1,3-dihydro-2H-3-benzazepin-2-on-3-yl]-3-[N-methyl-N-(6,7-dimethoxy-1,2,3,4-tetrahydronaphth-2-yl)-amino]-propane or its nontoxic, pharmaceutically acceptable addition salt.

5. Compound of claim 1 which is 1-[7,8-dimethoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane or its nontoxic, pharmaceutically acceptable addition salt.

6. A compound of claim 1 which is 1-[7,8-dimethoxy-1,3,4,5-tetrahydro-2H-3-benzazepin-2-on-3-yl]-3-[N-benzyl-N-(6,7-dimethoxy-1,2,3,4-tetrahydronaphth-2-yl)-amino]-propane or its nontoxic, pharmaceutically acceptable addition salt.

7. A compound of claim 1 which is 1-[7,8-dimethoxy-1,3,4,5-tetrahydro-2H-3-benzazepin-2-on-3-yl]-3-[N-(6,7-dimethoxy-1,2,3,4-tetrahydronaphth-2-yl)-amino]- propane or its nontoxic, pharmaceutically acceptable addition salt.

8. A compound of claim 1 which is 1-[7,8-dimethoxy-1,3,4,5-tetrahydro-2H-3-benzazepin-2-on-3-yl]-[N-methyl-N-(1,2,3,4-tetrahydronaphth-2-yl)-amino]-propane or its nontoxic, pharmaceutically acceptable addition salt.

9. A compound of claim 1 which is 1-[7,8-dimethoxy-1,3,4,5-tetrahydro-2H-3-benzazepin-2-on-3-yl]-3-[N-methyl-N-(5-methoxy-1,2,3,4-tetrahydronaphth-2-yl)-amino]-propane or its nontoxic, pharmaceutically acceptable addition salt.

10. A compound of claim 1 which is 1-[7,8-dimethoxy-1,3,4,5-tetrahydro-2H-3-benzazepin-2-on-3-yl]-3-[N-methyl-N-(7-methoxy-1,2,3,4-tetrahydronaphth-2-yl)-amino]-propane or its nontoxic, pharmaceutically acceptable addition salt.

11. A compound of claim 1 which is 1-[7,8-dimethoxy-1,3,4,5-tetrahydro-2H-3-benzazepin-2-on-3-yl]-3-[N-methyl-N-(6-methoxy-1,2,3,4-tetrahydronaphth-2-yl)-amino]-propane or its nontoxic, pharmaceutically acceptable addition salt.

12. A compound of claim 1 which is 1-[7,8-dimethoxy-1,3,4,5-tetrahydro-2H-3-benzazepin-2-on-3-yl]-3-[N-methyl-N-(8-methoxy-1,2,3,4-tetrahydronaphth-2-yl)-amino]-propane or its nontoxic, pharmaceutically acceptable addition salt.

13. A compound of claim 1 which is 1-[7,8-dimethoxy-1,3,4,5-tetrahydro-2H-3-benzazepin-2-on-3-yl]-3-[N-methyl-N-(5,6-dimethoxy-1,2,3,4-tetrahydronaphth-2-yl)-amino]-propane or its nontoxic, pharmaceutically acceptable addition salt.

14. A compound of claim 1 which is 1-[7,8-dimethoxy-1,3,4,5-tetrahydro-2H-3-benzazepin-2-on-3-yl]-3-[N-(1,2,3,4-tetrahydronaphth-2-yl)-amino]-propane or its nontoxic, pharmaceutically acceptable addition salt.

15. A compound of claim 1 which is 1-[7,8-dimethoxy-1,3,4,5-tetrahydro-2H-3-benzazepin-2-on-3-yl]-3-[N-(5-methoxy-1,2,3,4-tetrahydronaphth-2-yl)-amino]-propane or its nontoxic, pharmaceutically acceptable addition salt.

16. A compound of claim 1 which is 1-[7,8-dimethoxy-2,3,4,5-tetrahydro-1H-3-benzazepin-3-yl]-3-[N-methyl-N-(6,7-dimethoxy-1,2,3,4-tetrahydronaphth-2-yl)-amino]-propane or its nontoxic, pharmaceutically acceptable addition salt.

17. A compound of claim 1 which is 1-[7,8-dimethoxy-1,3,4,5-tetrahydro-2H-3-benzazepin-1,2-dion-3-yl]-3-[N-methyl-N-(6,7-dimethoxy-1,2,3,4-tetrahydronaphth-2-yl)-amino]-propane or its nontoxic, pharmaceutically acceptable addition salt.

18. A compound of claim 1 which is 1-[7,8-dimethoxy-1,3,4,5-tetrahydro-2H-3-benzazepin-2-thion-3-yl]-3-[N-methyl-N-(6,7-dimethoxy-1,2,3,4-tetrahydronaphth-2-yl)-amino]-propane or its nontoxic, pharmaceutically acceptable addition salt.

19. A compound of claim 1 which is 1-[7,8-dimethoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane or its nontoxic, pharmaceutically acceptable addition salt.

20. A compound of claim 1 which is 1-[1-hydroxy-7,8-dimethoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane or its nontoxic, pharmaceutically acceptable addition salt.

21. A compound of claim 1 which is 1-[7,8-dimethoxy-1,3,4,5-tetrahydro-2H-1,3-benzodiazepin-2-on-3-yl]-3-[N-methyl-N-(7-methoxy-1,2,3,4-tetrahydronaphth-2-yl)-amino]-propane or its nontoxic, pharmaceutically acceptable addition salt.

22. A compound of claim 1 which is 1-[7,8-dichloro-1,3,4,5-tetrahydro-2H-1,3-benzodiazepin-2-on-3-yl]-3-[N-methyl-N-(6,7-dimethoxy-1,2,3,4-tetrahydronaphth-2-yl)-amino]-propane or its nontoxic, pharmaceutically acceptable addition salt.

23. A compound of claim 1 which is 1-[7,8-dimethoxy-1,3,4,5-tetrahydro-2H-1,3-benzodiazepin-2-on-3-yl]-3-[N-methyl-N-(6,7-dimethoxy-1,2,3,4-tetrahydronaphth-2-yl)-amino]-propane or its nontoxic, pharmaceutically acceptable addition salt.

24. A compound of claim 1 which is 1-[7,8-dimethoxy-1,3,-dihydro-2H-3-benzazepin-3-yl]-3-[N-methyl-N-(6,7-dimethoxy-1,2,3,4-tetrahydronaphth-2-yl)-amino]-propane or its nontoxic, pharmaceutically acceptable addition salt.

25. A compound of claim 1 which is 1-[7,8-dimethoxy-1,3,4,5-tetrahydro-2H-3-benzazepin-2-on-3-yl]-3-[N-allyl-N-(6,7-dimethoxy-1,2,3,4-tetrahydronaphth-2-yl)-amino]-propane or its nontoxic, pharmaceutically acceptable addition salt.

26. A compound of claim 1 which is 1-[7,8-ethylenedioxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane or its nontoxic, pharmaceutically acceptable addition salt.

27. A compound of claim 1 which is 1-[7,8-methylenedioxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane or its nontoxic, pharmaceutically acceptable addition salt.

28. A compound of claim 1 which is 1-[7,8-dimethoxy-1,3,4,5-tetrahydro-2H-3-benzazepin-2-on-3-yl]-3-[N-methyl-N-(6,7-dichloro-1,2,3,4-tetrahydronaphth-2-yl)-amino]-propane or its nontoxic, pharmaceutically acceptable addition salt.

29. A compound of claim 1 which is 1-[7,8-dimethoxy-1,3,4,5-tetrahydro-2H-3-benzazepin-2-on-3-yl]-3-[N-methyl-N-(6,7-methylenedioxy-1,2,3,4-tetrahydronaphth-2-yl)-amino]-propane or its nontoxic, pharmaceutically acceptable addition salt.

30. A compound of claim 1 which is 1-[7,8-methylenedioxy-1,3,4,5-tetrahydro-2H-3-benzazepin-2-on-3-yl]-3-[N-methyl-N-(6,7-methylendioxy-1,2,3,4-tetrahydronaphth-2-yl)amino]-propane or its nontoxic pharmaceutically acceptable addition salt.

31. A compound of claim 1 which is 1-[7-bromo-8-methoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane or its nontoxic, pharmaceutically acceptable addition salt.

32. A compound of claim 1 which is 1-[7-chloro-8-methoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane or its nontoxic, pharmaceutically acceptable addition salt.

33. A compound of claim 1 which is 1-[7-nitro-8-methoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane or its nontoxic, pharmaceutically acceptable addition salt.

34. A compound of claim 1 which is 1-[7-amino-8-methoxy-1,3,4,5-tetrahydro-2H-3-benzazepin-2-on-3-yl]-3-[N-methyl-N-(6,7-dimethoxy-1,2,3,4-tetrahydronaphth-2-yl)-amino]-propane or its nontoxic, pharmaceutically acceptable addition salt.

35. A compound of claim 1 which is 1-[7,8-dimethoxy-1,3,4,5-tetrahydro-2H-1,3-benzodiazepin-2-on-3-yl]-3-[N-methyl-N-(6-methoxy-1,2,3,4-tetrahydronaphth-2-yl)-amino]-propane or its nontoxic, pharmaceutically acceptable addition salt.

36. A method of lowering heart rate in a human or animal in need thereof, which method comprises administering to said human or animal an effective amount of a compound of any of claims 1, 2 or 3.

37. A method of reducing the oxygen requirement of the heart in the human or animal in need thereof, which method comprises administering to said human or animal an effective amount of a compound of any of claims 1, 2 or 3.

38. A pharmaceutical composition for lowering heart rate and/or reducing the oxygen requirement of the heart in a human or animal, which composition comprises an effective amount of any of claims 1, 2 or 3 and a non-toxic, pharmaceutically acceptable carrier.

* * * * *